United States Patent [19]

Ammeraal et al.

[11] Patent Number: 5,194,094
[45] Date of Patent: Mar. 16, 1993

[54] FRACTIONATING STARCH HYDROLYSATES

[75] Inventors: Robert Ammeraal, Worth, Ill.; Gregory Delgado, E. Chicago, Ind.

[73] Assignee: American Maize-Products Company, Stamford, Conn.

[21] Appl. No.: 713,807

[22] Filed: Jun. 12, 1991

[51] Int. Cl.$^5$ .............................................. C08B 30/00
[52] U.S. Cl. ....................................... 127/69; 127/70; 127/71
[58] Field of Search ............................. 127/69, 70, 71

[56] References Cited

U.S. PATENT DOCUMENTS

| | | | |
|---|---|---|---|
| 4,781,977 | 11/1988 | Yagi et al. | 428/332 |
| 4,808,232 | 2/1989 | Beesley | 127/46.3 |
| 4,840,807 | 6/1989 | Yoshida et al. | 426/48 |
| 4,867,884 | 9/1989 | Rendleman | 210/635 |
| 4,916,064 | 4/1990 | Derez et al. | 127/30 |
| 5,007,966 | 4/1991 | Hedges et al. | 127/34 |
| 5,007,967 | 4/1991 | Ammeraal | 127/55 |

FOREIGN PATENT DOCUMENTS 0268997 of 0000 European Pat. Off. .

Primary Examiner—Theodore Morris
Assistant Examiner—P. L. Hailey
Attorney, Agent, or Firm—Lucas & Just

[57] ABSTRACT

A low DE starch hydrolysate is fractionated using a strong base ion exchange resin in hydrophobic anion form. Fractionated acyclic limit dextrins from a cyclodextrin glycosyl transferase digest are found to have extremely long term clarity.

17 Claims, No Drawings

FRACTIONATING STARCH HYDROLYSATES

The present invention relates to a process for fractionating starch hydrolysates having a low dextrose equivalent using a sorbent material that is a strong base ion exchange resin in hydrophobic anion form. Additionally, it has been found that the fractionated acyclic limit dextrin from a digest of cyclodextrin glycosyl transferase exhibits long term stability against haze at high concentrations.

Starch is thought to be made up of two types of polymers, amylose and amylopectin. Amylose is a polymer of D-glucose (anhydroglucose) wherein each glucose monomer is bound to another glucose monomer by an alpha 1,4-linkage. Amylopectin is a polymer of D-glucose wherein the glucose monomers are bound together by both alpha 1,4-linkages and alpha 1,6-linkages. The molecular weight of the amylopectin and amylose, the ratio of amylopectin to amylose, as well as the physical structure of the amylopectin varies depending on the plant from which the starch is extracted as well as the genetic background of the plant from which the starch is extracted. For example, some high amylose corn starch contains about 50% by weight amylose and 50% amylopectin while waxy corn starch contains about 99% by weight amylopectin.

Typically, starch is extracted from a plant in the form of a granule in which both amylose and amylopectin are intertwined to form the granule. In the case of corn starch, the kernel is milled to extract the starch granules and separate the starch granules from the other portions of the kernel in either a wet milling or dry milling process.

Starch hydrolysates are the product of the degradation of starch. Typically, starch is treated with either an acid or an enzyme so as to break down the polymeric structure into oligosaccharides. The degree of degradation is conventionally measured by the dextrose equivalent of the starch hydrolysate. Dextrose equivalent (DE) is an indication of the total reducing sugars in the starch hydrolysate calculated as D-glucose on a dry-weight basis. The DE is inversely related to the degree of polymerization (DP). Unhydrolyzed starch has a DE of about zero while glucose has a DE of 100 and a DP of 1 ($DP_1$). Starch hydrolysates having a DE less than about 20 are typically referred to as maltodextrins.

Where the enzyme used is a cyclodextrin glycosyl transferase (CGT), the starch digest contains not only cyclodextrins but also acyclic limit dextrins, and some sugars, glucose, maltose and triose. These acyclic limit dextrins are generally considered a by-product because the primary objective of treating starch with the CGT is to produce cyclodextrin.

One problem associated with low DE starch hydrolysates (DE 1-20) is variability of the molecular weight makeup of the hydrolysate. Fractionation provides a way to separate the starch hydrolysate into components of similar molecular weight or DP. Other methods for fractionating low DE starch hydrolysate with a sorbent material include using an OH-type anion exchange resin, see Japanese Patent Publication (Kokoko) No. 46290/1977 and gel-type filtering agents such as Amberlite IR 120 and Amberlite IRA 411, see U.S. Pat. No. 4,840,807, dated Jun. 20, 1989.

It has now been discovered that a low DE starch hydrolysate can be fractionated by means of a strong base ion exchange resin in hydrophobic anion form. It has also been discovered that an aqueous solution of acyclic limit dextrins fractionated by means of the process of the present invention from a CGT digest is stable for extremely long periods of time at high solids concentrations.

The acyclic limit dextrins from a CGT digest are suitable for use in a variety of food, pharamaceutical and industrial applications, and satisfy the need for a product having a relatively high viscosity, low sweetness, and an increased stability to haze. These acyclic limit dextrins from a CGT digest are useful for any application where increased thickness is desired together with a clear appearance. The product of such present invention can be used with food applications such as for pie fillings, jellies, syrups, and candies; in pharmaceutical applications for use in syrups such as cough syrups; and in industrial applications such as adhesives.

Strong base ion exchange resins in hydrophobic anion form have been used to separate cyclodextrins, see U.S. Pat. No. 4,808,232 dated Feb. 28, 1989, but it is surprising and unexpected that such a sorbent material will resolve acyclic dextrins. Further, it was surprising that these columns would accept heavy single loads of solids and acceptable fractionation could be achieved with about four column volumes of eluant water at flow rates of about 1 liter per hour through a 3 inch diameter column (26 cm/hour, linear velocity). This procedure was found superior to ultrafiltration and typical size exclusion chromatography, for removing smaller saccharides from a starch hydrolysate. Also, unrefined solids may be processed through a column of this type.

The process of the present invention provides for large loads and fast through-put rates while still obtaining acceptable separation. It has been found that high solids levels are possible, thereby minimizing the amount of water used and requiring little or no concentration prior to drying.

The process of the present invention comprises the steps of forming an aqueous slurry of starch hydrolysate; contacting the aqueous slurry of starch hydrolysates with a strong base ion exchange resin in hydrophobic anion form to fractionate the starch hydrolysate into different molecular weight fractions, and collecting the fractionated starch hydrolysate.

The step of forming an aqueous slurry of starch hydrolysate is accomplished in a conventional manner using conventional equipment. The starch hydrolysate can be formed by an acid treatment, an enzyme treatment or both.

The base starch is obtained from any plant source such as corn, wheat, rice or sorghum. The starch can be of the waxy variety, common or high amylose variety. Preferably corn starch is used, either common or waxy.

In order to acid treat the starch, an aqueous slurry of starch at about 5 to about 40% by weight starch is prepared. This slurry is reacted with acid, generally a strong acid, at a temperature above the gelatinization temperature of the starch. Such a procedure is preferably carried out by jet cooking the slurry through a conventional jet cooker with or without acid already in the slurry and then allowing the slurry to react with the acid, adding acid if needed, for a desired period of time or until the desired dextrose equivalent (DE) is reached. The DE is roughly proportional to the length of time for the reaction. Generally, such jet cooking destroys the starch's granular structure.

After acid treatment, the resulting slurry is neutralized. Suitable acids used to catalyze the hydrolysis reaction include hydrochloric acid and sulfuric acid.

In order to enzyme treat the starch, an aqueous slurry of starch is made up having about 5 to about 40% by weight starch. To this slurry, enzyme is added at the optimum pH and temperature for the enzyme. Some advantage is found by first jet cooking the slurry to open up the starch granules, cooling the slurry to optimum temperature for the enzyme and then adding the enzyme. If the enzyme is jet cook stable, then the enzyme can be added to the slurry prior to jet cooking. The slurry may also be treated with acid first to a low DE and then enzyme treated. Suitable enzymes include alpha-amylase, cyclodextrin glycosyl transferase (CGT) and beta-amylase.

Preferably, the hydrolysate slurry has been treated with carbon and an ion exchange resin in a conventional manner.

Carbon treatment of the starch hydrolysate slurry is accomplished using activated carbon to remove color, color precursors, and undesirable off-flavored materials. Carbon treatment removes most of the soluble proteinaceous material present and substantially all the 5-(hydroxymethyl)-2-furaldehyde formed during the acid treatment. Additionally, activated carbon is effective in the removal of heavy metals, such as iron and copper. Conventionally, carbon treatment is a 2- or 3-stage countercurrent batch application of activated powdered carbon or a counter-current application of activated granular carbon in cylindrical columns. Such operation is accomplished in a conventional manner.

Although carbon refining is adequate for purification of most conventional starch hydrolysate slurries, it is preferred to further treat the slurry by ion-exchange deionizer. Such treatment removes substantially all remaining soluble nitrogenous compounds, including amino acids and peptides that contribute color body formation via the Maillard reaction with reducing sugars.

A typical ion-exchange deionization system consists of fixed-bed columns. The cation-exchange resins used are strong acid exchangers (sulfonated resins in the hydrogen form), and the anion exchangers usually are weak base resins (tertiary amine in the free base form). The anion-exchange resins remove acids generated by reaction of the salts in the syrup liquor with the cation-exchange resins.

Where the enzyme is cyclodextrin glycosyl transferase (CGT), it is preferred that the starch hydrolysate solution be subjected to one or more steps to remove the cyclodextrins or a majority of the cyclodextrins produced by the enzyme. Such a process is conventional. Typically, the cyclodextrin product is removed by crystallization or complexation. The crystals or complexed cyclodextrin is then recovered, leaving behind an aqueous slurry of starch hydrolysate suitable for use in the present invention. The enzyme, CGT, is obtained from microorganisms such as *B. macerans, B. circulans, B. stearothermophilus* and *Bacillus sp.* (alkalophilic), as well as others. The parameters for the reaction between the selected CGT and the selected starch are conventional and well-described in the literature. Conventionally, the starch is slurried in aqueous solution at a concentration of up to about 35% by weight solid. It is then subjected to gelatinization and liquefaction by enzyme or acid to below 2.0 DE, preferably by enzyme. The preferred enzyme for liquefaction is bacterial alpha amylase.

After deactivating the liquefying enzyme by either heat or acid, the solution is treated with a selected CGT at the pH, temperature and time of treatment that is optimal for the selected CGT. Generally, the action of CGT on starch to produce cyclodextrins takes place at a pH between about 4.5 to about 8.5, at a temperature of about ambient to about 75° C., and for about 10 hours to about seven days. The amount of individual cyclodextrins, e.g. alpha, beta, and gamma, produced by the action of CGT on the starch will vary depending on the treatment conditions and CGT selected.

As mentioned above, a by-product of the process to prepare cyclodextrins is an aqueous slurry of starch hydrolysate which contains a variety of different types of acyclic limit dextrins. This by-product has been considered virtually unusable in the past because there was no satisfactory method known to fractionate the starch hydrolysate to obtain a product containing suitable dextrin of a particular molecular weight. It is exactly this by-product that is fractionated by the process of the present invention.

As disclosed in U.S. Pat. No. 4,808,232, issued Feb. 28, 1989, a strong base ion exchange resin in hydrophobic anion form can be used to separate cyclodextrins. This same material can be used to fractionate the starch hydrolysate.

In order to form the resin used in the present invention, a strong base ion exchange resin is converted into the anionic form in a conventional manner.

Strong base ion exchange resins are made up of a matrix material such as polystyrene which has usually been cross linked to a degree, 1-5%, and onto which a strong base such as trimethyl benzyl ammonium or dimethyl hydroxyethyl benzyl ammonium is bound. Suitable commercial resins include Dowex 1×2-400, Amberlite CG-400 and Dowex SBR. Good results have been obtained with Dowex 1×2-400.

The strong base ion exchange resin is then converted into anionic form in a conventional manner using conventional equipment. Suitable anions include benzoate, phenolphthalein, disodium salt and salicylate. Good results have been obtained with the benzoate anion. The anion is in any form which allows for the conversion. Suitable benzoate salts include sodium benzoate, potassium benzoate and ammonium benzoate.

Contacting the low DE starch hydrolysate with the strong base ion exchange resin in hydrophobic anionic form is accomplished in a conventional manner using conventional equipment. Specifically, either a fixed bed or continuous countercurrent (simulated moving bed) system is used. Good results have been obtained with a fixed bed. In a fixed bed operation, a vertical column is packed with the strong base ion exchange resin in hydrophobic anionic form. The low DE starch hyrolysate enters at the top of the column and flows through the column. Water is also added to the top of the column to help move the hydrolysate through the column. While passing through the column the hydrolysate fractionates so that the dextrins which emerge in the eluant at the bottom of the column are grouped by molecular weight and size.

The temperature of the column is ambient or slightly above ambient, 20° C. to 100° C. Good results have been found at ambient temperature, about 25° C. Good results have also been found by allowing the starch hydrolysate to flow through a vertical column without the addition of pressure to move the hydrolysate through the column.

Preferably, the solids level of the starch hydrolysate before contacting the strong base ion exchange resin in tion and two by an acid catalyzed hydrolysis reaction. Table A reports the results from fractionation.

TABLE A

| Sample No. | I | II | III | IV | V |
|---|---|---|---|---|---|
| Starch base | waxy corn | waxy corn | common corn | high amylose corn | common corn |
| Catalyst(s) | a) amylase[3] b) CGT[1] | amylase[3] | acid[4] | amylase[3] | acid[4] and dry heat |
| Schoorl DE | 10.4 | 5.2 | 15.5 | 10.6 | 5.6 |
| % DP1-12 | 21.7% | 8.8% | 44.2% | 39.3% | 4.1% |
| Sample loaded | | | | | |
| volume (ml) | 3090 | 1415 | 1065 | 1159 | 1010 |
| % solids | 20.7 | 25.7 | 13.0 | 8.1 | 13.5 |
| dry weight (%) | 691.6 | 400 | 145.4 | 96.1 | 143.2 |
| eluant % solids | 12.7 | 7.3 | 4.8 | 3.1 | 4.5 |
| Fractions Collected | | | | | |
| 1. eluant volume (ml) | 0–1000 | 0–300 | 0–1000 | 0–1000 | 0–1000 |
| Grams | 88.2 | 29.4 | 42.1 | 29.9 | 70.6 |
| % recovered (by wt.) | 16.6 | 7.4 | 29.0 | 31.1 | 49.3 |
| DE | 1.31 | .38 | 1.89 | 3.55 | 1.58 |
| % DP1-12 | 0 | 0 | 0 | 2.87 | 0 |
| 2. eluant volume (ml) | 1000–2000 | 300–1000 | 1000–2000 | 1000–2000 | 1000–2000 |
| Grams | 133.4 | 124.7 | 85.6 | 51.0 | 56.4 |
| % recovered | 25.1 | 31.2 | 58.9 | 53.1 | 39.4 |
| DE | 7.19 | .58 | 14.86 | 14.21 | 7.29 |
| % DP1-12 | 10.39 | 0 | 54.33 | 57.26 | 4.55 |
| 3. eluant volume (ml) | 2000–3000 | 1000–2000 | 2000–3000 | 2000–3000 | 2000–3000 |
| Grams | 225.8 | 132.4 | 17.4 | 11.6 | 9.0 |
| % recovered | 42.4 | 33.1 | 12.0 | 12.1 | 6.3 |
| DE | 11.73 | 5.62 | 42.4 | 25.9 | 24.9 |
| % DP1-12 | 21.89 | 11.33 | 96.2 | 97.1 | 73.4 |
| 4. eluant volume (ml) | 3000–4000 | 2000–5000 | — | — | — |
| Grams | 84.8 | 87.4 | — | — | — |
| % recovered | 15.9 | 21.9 | — | — | — |
| DE | 21.57 | 11.78 | — | — | — |
| % DP1-12 | 61.8 | 37.8 | — | — | — |
| Elution Profile[2] | | | | | |
| void volume (L) | 1.0 | 1.0 | 1.2 | 1.2 | 1.1 |
| elution volume (L) | 6.0 | 5.0 | 3.0 | 3.0 | 3.0 |
| peak volume (L) | 3.2 | 1.7 | 2.4 | 2.2 | 2.0 |
| M.W. rank | 1 (lowest) | 5 | 2 | 3 | 4 |

[1] cyclodextrin glycosyl transferase
[2] elution profiles were constructed with intermittent solids monitoring and values listed are best estimates
[3] bacterial alpha-amylase
[4] hydrochloric acid hydrophobic anion form has a concentration of about 10 to about 30% by weight.

It has been found that the longer dextrins emerge first from the column.

The limit dextrins produced by the process of the present invention from a CGT digest and which have stability against haze have a DP of about 10 to about 100, and are acyclic limit dextrins. Limit dextrins are dextrins to which the enzyme no longer catalyzes the hydrolysis reaction. The limit dextrins from the CGT digest which are part of the present invention are acyclic, linear, as opposed to the cyclic dextrins, cyclodextrins, which are also contained in the CGT digest.

Preferably, the fractionated acyclic limit dextrin product of the present invention is about 95% by weight free of cyclodextrin and, more preferably, about 99% by weight free of cyclodextrins.

The preferred source of starch for these acyclic limit dextrins is a waxy corn starch which has been converted to about 5 DE by bacterial alpha-amylase prior to treatment by CGT.

These and other aspects of the present invention may be more fully understood by reference to the following examples.

EXAMPLE I

Five different starch hydrolysate syrups were prepared, three by an enzyme catalyzed hydrolysis reaction and two by an acid catalyzed hydrolysis reaction.

The strong base ion exchange resin in hydrophobic anion form was prepared by slurrying 2.5 kg. of Dowex-1-Chloride, strongly basic anion exchange resin (Dowex 1×2-400 mesh) in water and pouring it into a glass chromatography column three inches in diameter. A glass wool plug covered with a layer of sand supported the Dowex bed. The bed depth was about 70 cm. The column had about 3 liters total volume, 1 liter void volume. After washing with water, a 0.5N sodium benzoate solution was pumped through the column until breakthrough. The column held an estimated 332 gms. of benzoate ion or about 2.74 moles. The column was washed with deionized water before use.

Deionized water was the eluant and the flow rate typically varied from 10–20 ml/min. Flow rate up to 30 ml/min. was possible with water. With sample on the column the flow rate depended on the sample size and viscosity and was as low as 7 ml/min. Bed surface area was 45.6 cm[2]. Elution was done at ambient temperature.

Typically one liter (one void volume) fractions were collected and the total sample was collected in 3 to 5 liters.

The total dilution of the sample during the separation was about 30%.

The syrups in Samples I, II, III and IV were carbon bleached with about 2% powdered carbon and then subjected to an ion exchange treatment over a mixed bed resin (mixed bed/iwt universal) before application to the fractionation column. The syrups in Samples II, III and IV were heated before application, cooled quickly and then applied to the column at 8 to 14% solids. The samples were heated to remove existing haze.

Sample I used a syrup from a commercial cyclodextrin process, the concentrated filtrate from the cyclodextrin crystallization liquid. The syrup contained some residual cyclodextrins. About 532.2 gms. of acyclic limit dextrins were recovered, during chromatography, from this syrup. The initial DE and percent DP1-12 for this material was a weighted average of the four fractions obtained during chromatography and the percent recovery for the individual fractions was based on recovered solids.

In Sample I the sample volume was nearly three times the void volume but fraction 1 contained no detectable DP1-12 oligosaccharides. This was typical for fraction 1 chromatograms in the other samples. Sample IV showed low levels of DP7-12 oligosaccharides in fraction 1 but no DP1-6 oligosaccharides. Fraction 1 was typically below 2DE, dependent on the material fractionated. In Sample II two fractions were collected in the first liter and neither had DP1-12 but they were different in DE and viscosity; indicating molecular weight fractionation extending into this volume. The total yield in Sample II of carbohydrate free of DP1-12 oligosaccharides was 154.1 gms. or 38.5% of the material loaded.

Other fractions were intermediate in DE and percent DP1-12 oligosaccharides between the first and last fractions. Most of these are not much different from available syrups, in chromatographic profile or DE. Two exceptions were fractions 3 of Samples III and IV which contained over 96% DP1-12 oligosaccharides, one at 42 DE and one at 26 DE.

Elution profiles were constructed from solids determinations at frequent intervals and elution peaks were estimated. Peak volumes were measured from application of the sample and include the void volume. The hydrolysates were ranked according to molecular weight based on degree of conversion, starch type, iodine color and viscosity. As shown in the table, this ranking is related to the peak volume.

EXAMPLE 2

This example illustrates the long term stability against haze of the fractionated acyclic limit dextrins from a CGT digest.

Fraction 3 of Sample I in Example 1 was concentrated to three solid levels, 64, 71 and 74 and stored at 4° C. for about one year. Both clarity and color were recorded for the three solids levels and are reported in Table B below.

TABLE B

| Solids | Clarity | | | Color | | |
|---|---|---|---|---|---|---|
| Day | 64 | 71 | 74 | 64 | 71 | 74 |
| 0 | 92 | — | — | 1.35 | — | — |
| 4 | 90 | — | — | 1.45 | — | — |
| 5 | 91 | — | — | 1.43 | — | — |
| 6 | 90 | — | — | 1.43 | — | — |
| 10 | 90 | 91 | — | 1.38 | 1.78 | — |
| 11 | 90 | 90 | — | 1.38 | 1.75 | — |
| 12 | 90 | 91 | — | 1.43 | 1.78 | — |
| 13 | 90 | 90 | — | 1.45 | 1.78 | — |
| 14 | 90 | 90 | — | 1.48 | 1.80 | — |
| 17 | 90 | 90 | 89 | 1.50 | 1.82 | 2.00 |
| 18 | 90 | 90 | 89 | 1.45 | 1.80 | 1.90 |

TABLE B-continued

| Solids | Clarity | | | Color | | |
|---|---|---|---|---|---|---|
| Day | 64 | 71 | 74 | 64 | 71 | 74 |
| 21 | 90 | 91 | 90 | 1.60 | 1.85 | 1.93 |
| 31 | 90 | 91 | 90 | 1.65 | 1.93 | 1.93 |
| 52 | 88 | 91 | 90 | 1.88 | 1.95 | 2.03 |
| 61 | 88 | 92 | 90 | 1.90 | 1.90 | 1.98 |
| 93 | 84 | 89 | 89 | 2.40 | 2.12 | 2.15 |
| 123 | 78 | 88 | 89 | 3.12 | 2.25 | 2.28 |
| 185 | 53 | 84 | 88 | 5.75 | 2.90 | 2.63 |
| 221 | 35 | 82 | 87 | 8.10 | 3.25 | 2.73 |
| 313 | — | 63 | 82 | — | 5.58 | 3.10 |
| 373 | — | 56 | 79 | — | 6.80 | 2.75 |

The clarity numbers are the percent of light at a wave length of 600 nm transmitted through a 4 cm cuvette at the indicated solids levels as compared to a 4 cm cell containing deionized water at the same wave length. The color is the difference between the absorbence (optical density) at 450 nm and 600nm multiplied by 100 and divided by the light path length of the cuvette (4 cm) at the various solids levels, i.e. color=$[A_{450} - A_{600}] \times 100]/4$ cm. Such measurements were made spectrophotometrically.

As will be appreciated by those in the art, a starch hydrolysate, claimed to have exceptional clarity, having a DE of about 10 and made by the hydrolysis of bacterial alpha-amylase on waxy corn starch had a percent transmittance at 65% solids at 600 nm of about 80% after 5 days storage at 4° C. The starch hydrolysate produced by the present invention has extremely long stability against haze. Based on the data in Table B, the starch hydrolysate of about 10 DE from the CGT digest obtains a percent transmittance of 80% after 114 days, 221 days and 334 days for the respective solids levels of 64, 71 and 74.

It will be understood that the claims are intended to cover all changes and modifications of the preferred embodiments of the invention herein chosen for the purpose of illustration which do not constitute a departure from the spirit and scope of the invention.

What is claimed is:

1. A process for fractionating a low DE starch hydrolysate of acyclic dextrins only comprising the steps of:
   (a) forming an aqueous slurry of a starch hydrolysate comprising acyclic dextrins and having a DE between about 1 to about 20;
   (b) contacting the aqueous slurry of starch hydrolysate of acyclic dextrins with a strong base ion exchange resin in hydrophobic anion form to fractionate the acyclic dextrins in the starch hydrolysate into different molecular weight fractions; and
   (c) collecting the fractionated acyclic dextrins only into different molecular weight fractions.

2. The process of claim 1 wherein said aqueous slurry of starch hydrolysate of acyclic dextrins is formed by the treatment of an acid on an aqueous slurry of starch.

3. The process of claim 1 wherein said aqueous slurry of starch hydrolysate of acyclic dextrins is formed by treatment of an enzyme on an aqueous slurry of starch.

4. The process of claim 3 wherein the enzyme is selected from the group consisting of alpha-amylase, cyclodextrin glycosyl transferase, and beta-amylase.

5. The process of claim 1 wherein said aqueous slurry of starch hydrolysate of acyclic dextrins is formed by first contacting a base slurry of starch hydrolysate with a cyclodextrin transferase to produce both cyclodextrins and acyclic dextrins; and subsequently separating the cyclodextrin from the aqueous starch hydrolysate slurry to leave acyclic dextrins in solution.

6. The process of claim 1 wherein the step of contacting the aqueous slurry of starch hydrolysate of acyclic dextrins with a strong base ion exchange resin in hydrophobic anion form is done using a column packed with a resin and the slurry is added to the top of the column and allowed to flow down through the column.

7. The process of claim 6 wherein water is added to the top of the column after the slurry.

8. An acyclic starch hydrolysate having a DE between about 1 to about 20, obtained from a cyclodextrin glycosyl transferase digest, said starch hydrolysate producing an aqueous slurry having a long term clarity of about 80% transmittance at a solids level of about 65% by weight after storage at 4° C. for a period of five days measured spectrophotometrically at a wavelength of 600 nm through a cuvette with a light path of 4 cm, wherein the acyclic starch hydrolysate is acyclic limit dextrins and some glucose, maltose and triose from the digest.

9. The starch hydrolysate of claim 8 wherein the starch is a waxy starch hydrolysate.

10. A process for fractionating acyclic dextrins only comprising the steps of:
  (a) forming a slurry comprising acyclic dextrins wherein said slurry is an aqueous slurry of starch hydrolysates having a DE between about 1 to about 20 and said slurry has been obtained from the treatment of an acid and/or an enzyme on the starch;
  (b) passing said slurry of acyclic dextrins through a matrix of a strong base ion exchange resin in hydrophobic anion form to fractionate the acyclic dextrins into different molecular weight fractions; and
  (c) eluting the fractionated acyclic dextrins and recovering the fractionated acyclic dextrins only by different molecular weights.

11. The process of claim 10 wherein said acid is selected from the group consisting of hydrochloric acid and sulfuric acid.

12. The process of claim 10 wherein said acid is selected from the group consisting of alpha-amylase, cyclodextrin glycosyl transferase and beta-amylase.

13. The process of claim 10 wherein water is used for eluting the fractionated acyclic dextrins.

14. The process of claim 10 wherein the step of forming said slurry comprises the steps of:
  (a') treating an aqueous slurry of a base starch with bacterial alpha-amylase to produce a starch hydrolysate with a DE below 2.0;
  (a") treating the hydrolysate with a DE below 2.0 with a cyclodextrin glycosyl transferase to produce an aqueous mixture containing both cyclodextrins and acyclic dextrins; and
  (a''') removing the cyclodextrins from the slurry to leave the slurry comprising acyclic dextrins having a DE between about 1 to about 20.

15. Acyclic dextrins only obtained from the process of claim 14, said dextrins producing an aqueous slurry having a long term clarity of about 80% transmittance at a solids level of about 65% by weight after storage at 4° C. for a period of five days measured spectrophotometrically at a wavelength of 600 nm through a cuvette with a light path of 4 cm.

16. The acyclic dextrins of claim 15 wherein the base starch is a waxy starch.

17. Acyclic dextrins only obtained from the process of claim 10 wherein said aqueous starch hydrolysate is obtained from a cyclodextrin glycosyl transferase digest, said acyclic dextrins producing an aqueous slurry having a long term clarity of about 80% transmittance at a solids level of about 65% by weight after storage at 4° C. for a period of five days measured spectrophotometrically at a wavelength of 600 nm through a cuvette with a light path of 4 cm.

* * * * *

UNITED STATES PATENT AND TRADEMARK OFFICE
CERTIFICATE OF CORRECTION

PATENT NO. : 5,194,094
DATED : March 16, 1993
INVENTOR(S) : Robert N. Ammeraal et al.

It is certified that error appears in the above-identified patent and that said Letters Patent is hereby corrected as shown below:

Column 3, line 65, change "solid" to --solids--.

Table A (columns 5 and 6), line 12 thereof, after "dry weight (%)" insert --final average--.

Column 8, line 62 (claim 4), change "the" to --said--.

Column 9, line 8 (claim 6), change "a" to --the--;
line 14 (claim 8), after "said" insert --acyclic--.

Column 10, line 4 (claim 12), change "said acid" to --the enzyme--;
line 27 (claim 15), change "alight" to --a light--.

Signed and Sealed this

Sixteenth Day of November, 1993

Attest:

BRUCE LEHMAN

Attesting Officer                Commissioner of Patents and Trademarks